(12) United States Patent
Suzuki

(10) Patent No.: US 10,000,657 B2
(45) Date of Patent: Jun. 19, 2018

(54) FLUORINE-CONTAINING URETHANE (METH)ACRYLATE, CURABLE COMPOSITION, AND ANTIREFLECTIVE FILM

(71) Applicant: DIC Corporation, Tokyo (JP)

(72) Inventor: Hideya Suzuki, Ichihara (JP)

(73) Assignee: DIC Corporation, Tokyo (JP)

( * ) Notice: Subject to any disclaimer, the term of this patent is extended or adjusted under 35 U.S.C. 154(b) by 307 days.

(21) Appl. No.: 14/913,672

(22) PCT Filed: Aug. 19, 2014

(86) PCT No.: PCT/JP2014/071622
§ 371 (c)(1),
(2) Date: Feb. 22, 2016

(87) PCT Pub. No.: WO2015/025836
PCT Pub. Date: Feb. 26, 2015

(65) Prior Publication Data
US 2016/0208131 A1 Jul. 21, 2016

(30) Foreign Application Priority Data
Aug. 23, 2013 (JP) .................. 2013-173415

(51) Int. Cl.
| | |
|---|---|
| *C09D 135/02* | (2006.01) |
| *C07C 271/16* | (2006.01) |
| *C08F 20/38* | (2006.01) |
| *C08F 20/36* | (2006.01) |
| *G02B 1/11* | (2015.01) |
| *C09D 4/00* | (2006.01) |
| *G02B 1/111* | (2015.01) |
| *G02B 1/14* | (2015.01) |
| *C09D 133/16* | (2006.01) |
| *C09D 133/18* | (2006.01) |
| *C08F 222/10* | (2006.01) |

(52) U.S. Cl.
CPC .......... *C09D 135/02* (2013.01); *C07C 271/16* (2013.01); *C08F 20/36* (2013.01); *C08F 20/38* (2013.01); *C09D 4/00* (2013.01); *C09D 133/16* (2013.01); *C09D 133/18* (2013.01); *G02B 1/11* (2013.01); *G02B 1/111* (2013.01); *G02B 1/14* (2015.01); *C08F 2222/1086* (2013.01)

(58) Field of Classification Search
CPC ..... C07C 271/00–271/68; C08F 20/00–20/70; G02B 1/00–1/18; C09D 4/00; C09D 135/02; C09D 133/16; C09D 133/18
See application file for complete search history.

(56) References Cited

U.S. PATENT DOCUMENTS

2011/0059302 A1 3/2011 Kodama

FOREIGN PATENT DOCUMENTS

| JP | 2008-115258 A | | 5/2008 |
|---|---|---|---|
| JP | 2009-167354 A | | 7/2009 |
| JP | 2009167354 A | * | 7/2009 |
| JP | 2009167357 A | * | 7/2009 |

OTHER PUBLICATIONS

Machine translation of JP2008115258. Retrieved Feb. 14, 2018.*
Machine translation of JP2009167354. Retrieved Feb. 14, 2018.*
Machine translation of JP2009167357. Retrieved Feb. 14, 2018.*
International Search Report dated Nov. 18, 2014, issued for PCT/JP2014/071622.

\* cited by examiner

*Primary Examiner* — Prashant J Khatri
(74) *Attorney, Agent, or Firm* — Locke Lord LLP

(57) ABSTRACT

It is an object of the present invention to provide a urethane (meth)acrylate that enables formation of a cured layer having a low reflectance and excellent excoriation resistance, a curable composition produced by using the same, and an antireflective film. In particular, there is provided a fluorine-containing urethane (meth)acrylate represented by General Formula (I) and having a fluorine atom content ranging from 25 to 60 mass % (where $R_1$ and $R_2$ each represent a specific fluorinated alkyl group, $R_3$ and $R_4$ each represent a hydrogen atom or a methyl group, A represents a trivalent linking group represented by any of Structural Formulae (A1) to (A4), and X and Y each independently represent a divalent linking group represented by any of Structural Formulae (a) to (c)) [in Structural Formula (c), R5 represents an alkyl group having 1 to 6 carbon atoms].

9 Claims, 3 Drawing Sheets

FLUORINE-CONTAINING URETHANE (METH)ACRYLATE, CURABLE COMPOSITION, AND ANTIREFLECTIVE FILM

TECHNICAL FIELD

The present invention relates to a fluorine-containing urethane (meth)acrylate that enables formation of an antireflective layer that is a cured coating film having a low reflectance and excellent excoriation resistance as well, a curable composition that can be prepared by using the same, and an antireflective film.

BACKGROUND ART

In recent years, liquid crystal displays have been more likely to be used not only indoors but also outdoors. Liquid crystal displays therefore further need to have antireflective properties (decreased reflectance) in order to prevent the screens thereof from reflecting natural light than before. In liquid crystal displays used indoors, pixel density has been increased to show high-definition images as in 4K-TVs because of demands for better image quality, which raises the need for improved antireflective properties.

In order to give antireflective properties to the surface of a liquid crystal display, for example, a low reflection layer (LR layer) is disposed as the surface layer of a polarizing plate that serves as the outermost layer of the screen of the liquid crystal display. A composition used for forming the LR layer contains hollow silica particles to decrease the refractive index of the layer in many cases. In the case where the amount of the hollow silica particles is in excess in an attempt to further decrease the refractive index, however, the amount of a binder resin used for fixing the hollow silica particles in the composition becomes insufficient relative to the amount of the hollow silica particles, which causes a problem in which the LR layer is less likely to have an enough excoriation resistance. It is therefore effective to use a curable binder resin and to decrease the refractive index of this binder resin as much as possible in order to form an LR layer having an excoriation resistance and excellent antireflective properties.

In a known technique that is deemed to be most effective for decreasing the refractive index of a binder resin, a fluorine atom is introduced to the binder resin. A known example of a composition containing such a binder resin is a curable composition containing a polyfunctional acrylate having a fluorinated alkyl group and a cyclic aliphatic structure (for example, see Patent Literature 1). A known composition used for forming an LR layer is a curable composition containing a coating binder resin that is a mono(meth)acrylate having two fluorinated alkyl groups, a urethane bond, and a (meth)acryloyl group, although not directly disclosed (for instance, see Patent Literature 2). Such disclosed curable compositions containing a polyfunctional acrylate or mono(meth)acrylate, however, are insufficient for formation of a cured coating film having a sufficiently low refractive index and excellent excoriation resistance.

CITATION LIST

Patent Literature

PTL 1: Japanese Unexamined Patent Application Publication No. 2009-167354

PTL 2: Japanese Unexamined Patent Application Publication No. 2008-115258

SUMMARY OF INVENTION

Technical Problem

It is an object of the present invention to provide a polymerizable monomer that contains a fluorine atom and that enables formation of an antireflective layer that is a cured coating film having a low reflectance and excellent excoriation resistance as well, a curable composition that can be prepared by using the same and that is suitable for use in an antireflective coating material, and an antireflective film.

Solution to Problem

The inventors have intensively studied to achieve the above-mentioned object and found the following to accomplish the present invention: a urethane(meth)acrylate that is a (meth)acrylate having a urethane bond, that has two fluorinated alkyl groups and two (meth)acryloyl groups with the urethane bond interposed therebetween, and that contains a certain amount of fluorine atoms can be used to produce a curable composition which enables formation of a cured coating film having a low refractive index; a cured coating film having a low light reflectance can be formed without an excessive increase in the amount of hollow silica particles; and the amount of a polymerizable unsaturated group in the composition can be relatively large, so that the excoriation resistance of a cured coating film to be formed can be enhanced.

In particular, the present invention provides a fluorine-containing urethane (meth)acrylate represented by General Formula (I) and having a fluorine atom content ranging from 25 to 60 mass %.

[Chem. 1]

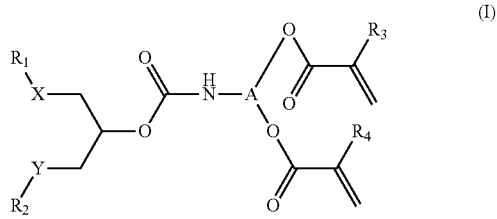

(where $R_1$ and $R_2$ each independently represent a fluorinated alkyl group in which the number of carbon atoms to which fluorine atoms are directly bonded is from 2 to 6 or a fluorinated alkyl group which has a bond via an oxygen atom and in which the number of carbon atoms to which fluorine atoms are directly bonded is from 2 to 6 in total; $R_3$ and $R_4$ each represent a hydrogen atom or a methyl group; A represents a trivalent linking group represented by any of Structural Formulae (A1) to (A4); and X and Y each independently represent a divalent linking group represented by any of Structural Formulae (a) to (c))

[Chem. 2]

-continued

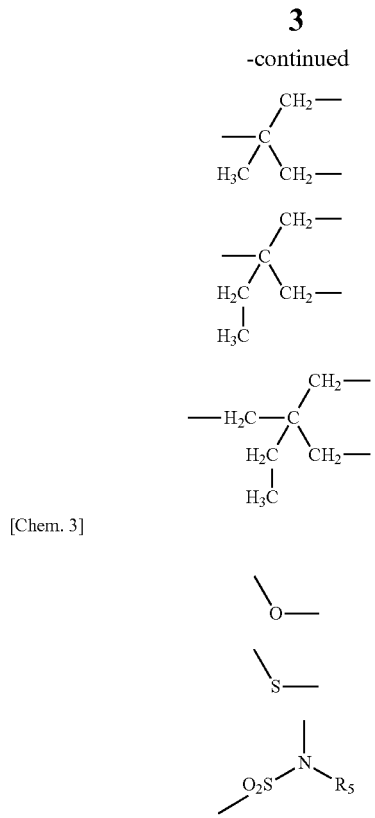

[Chem. 3]

[in Structural Formula (c), R5 represents an alkyl group having 1 to 6 carbon atoms]

The present invention also provides a curable composition that contains the fluorine-containing urethane (meth)acrylate (I).

The present invention also provides an antireflective film including a cured coating film of the curable composition.

Advantageous Effects of Invention

The fluorine-containing urethane (meth)acrylate of the present invention can be used to form a cured coating film having a low reflectance and excellent excoriation resistance. Thus, the fluorine-containing urethane (meth)acrylate of the present invention can be used to suitably prepare an antireflective coating composition.

DESCRIPTION OF EMBODIMENTS

Figure 1:
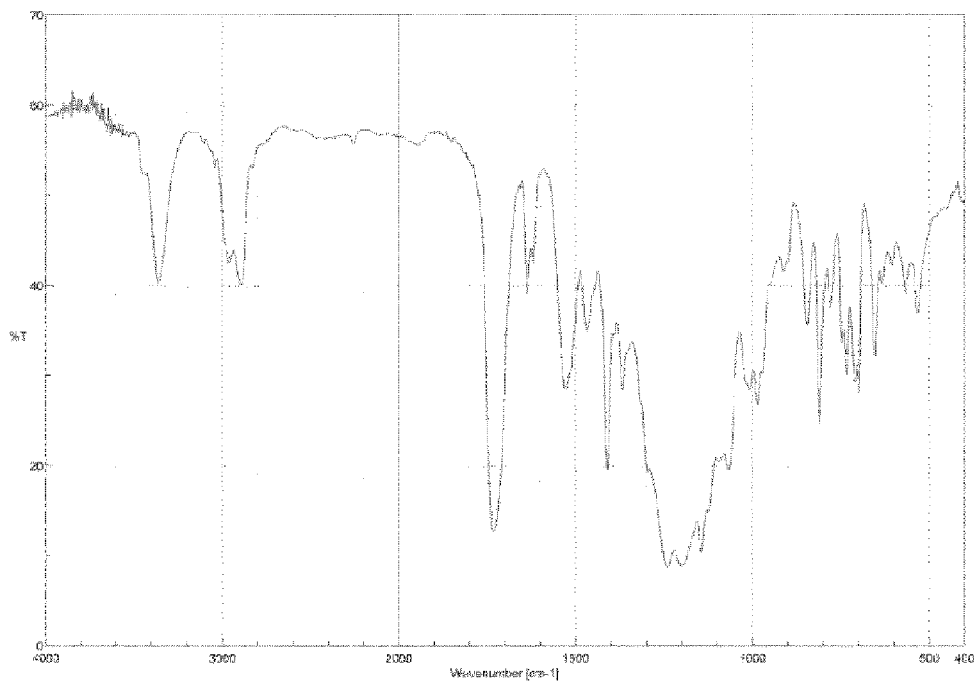
FIG. 1 is a chart illustrating the IR spectrum of a fluorine-containing urethane (meth)acrylate (1) obtained in Example 1.

The fluorine-containing urethane (meth)acrylate of the present invention has the following structure.

[Chem. 4]

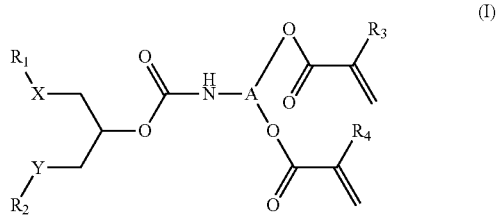

($R_1$ and $R_2$ each independently represent a fluorinated alkyl group in which the number of carbon atoms to which fluorine atoms are directly bonded is from 2 to 6 or a fluorinated alkyl group which has a bond via an oxygen atom and in which the number of carbon atoms to which fluorine atoms are directly bonded is from 2 to 6 in total; $R_3$ and $R_4$ each represent a hydrogen atom or a methyl group; A represents a trivalent linking group represented by any of Structural Formulae (A1) to (A4); and X and Y each independently represent a divalent linking group represented by any of Structural Formulae (a) to (c))

[Chem. 5]

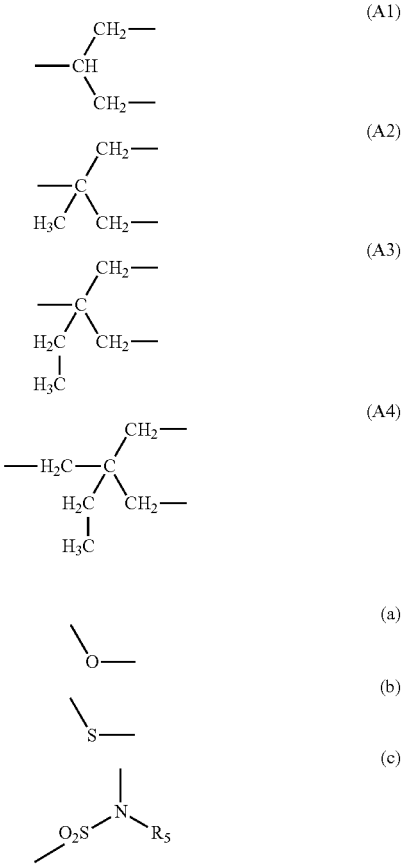

[Chem. 6]

[in Structural Formula (c), R5 represents an alkyl group having 1 to 6 carbon atoms]

The fluorine-containing urethane (meth)acrylate of the present invention has a fluorine atom content ranging from 25 to 60 mass %. A fluorine atom content of less than 25 mass % is not preferred because a cured coating film having a low refractive index is less likely to be formed. A fluorine atom content of greater than 60 mass % is also not preferred because crosslink density is decreased with the result that the strength of a cured coating film is impaired. The fluorine atom content is preferably in the range of 30 to 60 mass %, more preferably 35 to 60 mass %, and further preferably 40 to 55 mass %.

Each of $R_1$ and $R_2$ in the structure of the fluorine-containing urethane (meth)acrylate of the present invention needs to be a fluorinated alkyl having 2 to 6 carbon atoms. A fluorinated alkyl having one carbon atom does not bring a low refractive index. A fluorinated alkyl having seven or more carbon atoms is not preferred because it causes a product decomposed in the environment to be accumulated in a living body.

$R_1$ and $R_2$ are preferably each independently a fluorinated alkyl group in which the number of carbon atoms to which the fluorine atoms are directly bonded is from 4 to 6 because they enable the urethane (meth)acrylate to have a lower refractive index.

Examples of the fluorine-containing urethane (meth)acrylate of the present invention include fluorine-containing urethane (meth)acrylates represented by the following structural formulae.

[Chem. 7]

I-1

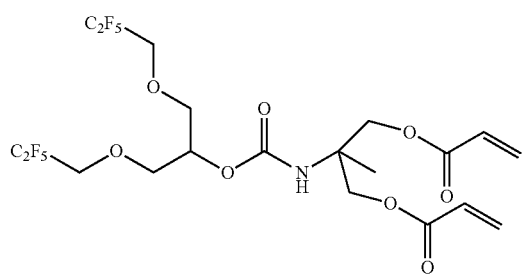

I-2

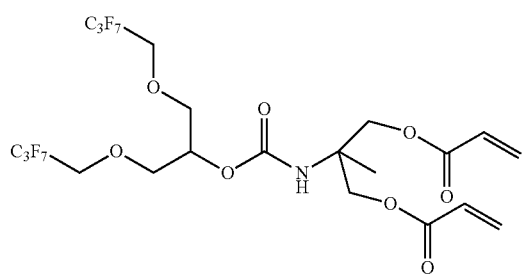

[Chem. 8]

I-3

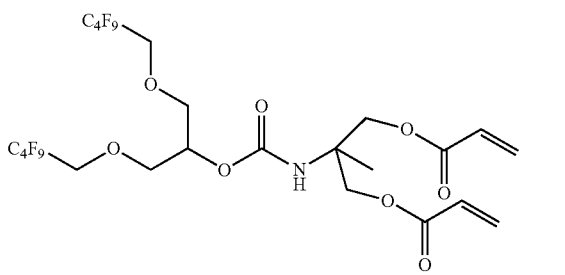

I-4

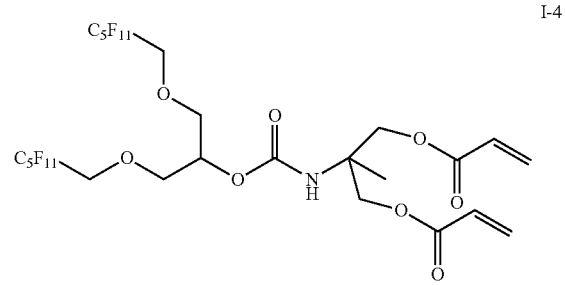

I-5

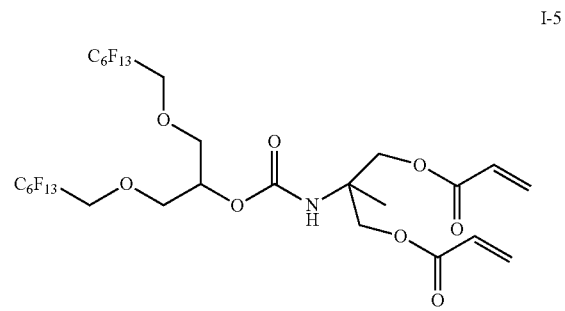

I-6

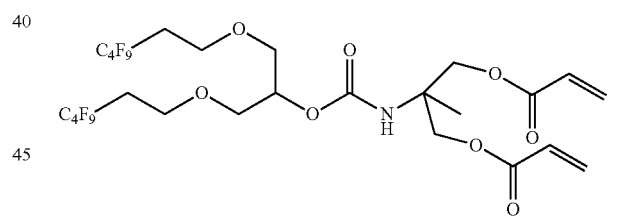

I-7

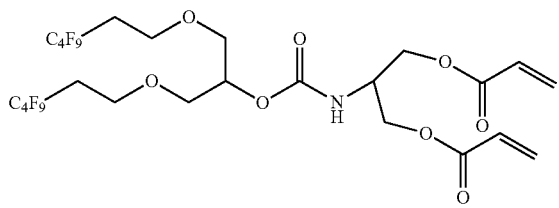

I-8

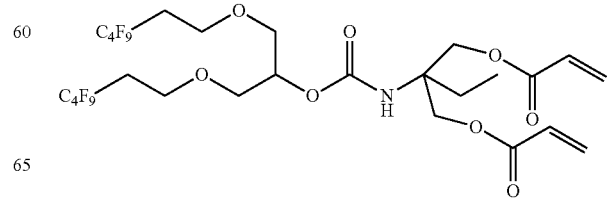

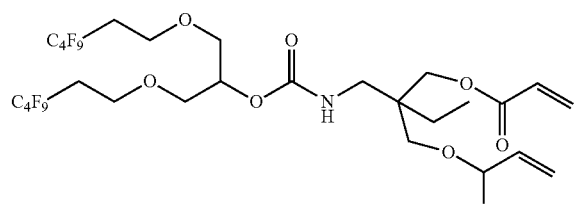

I-21
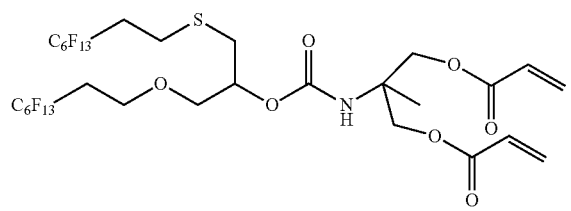
I-22
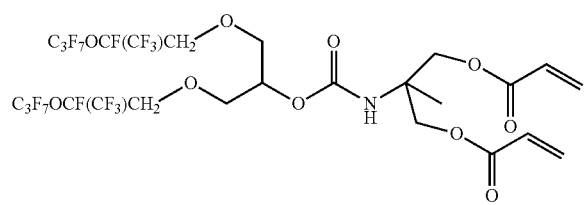
[Chem. 12]
I-23
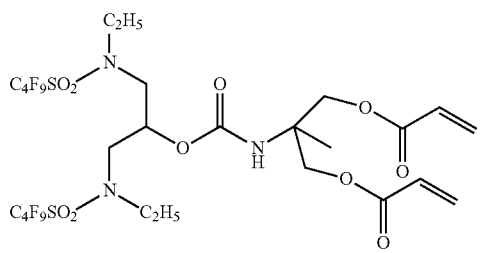
I-24
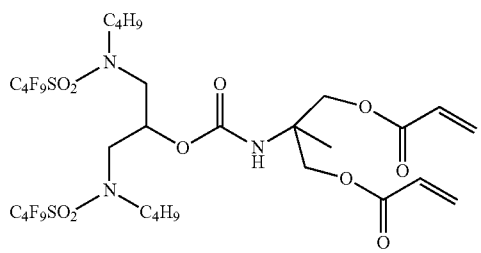
I-25
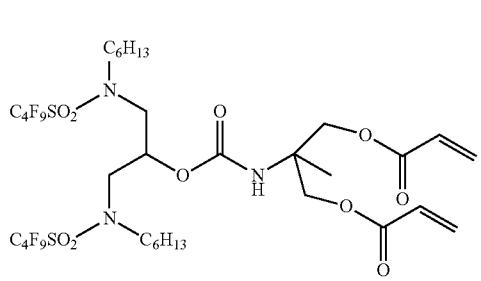
[Chem. 13]
I-26
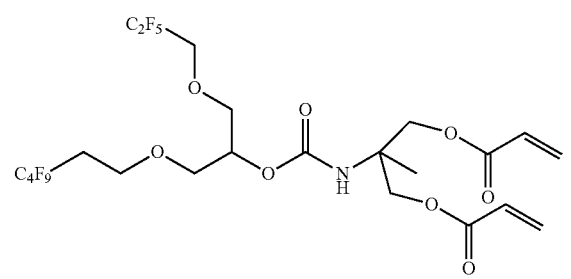
I-27
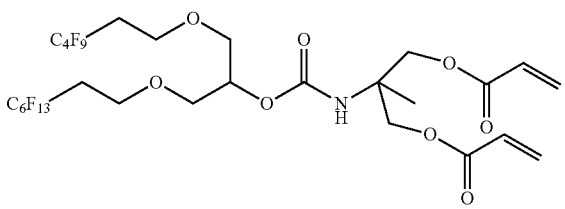
I-28
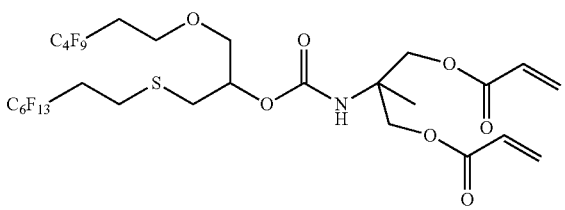
I-29
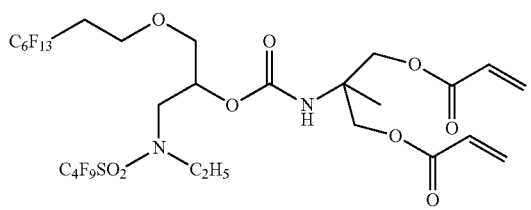
I-30
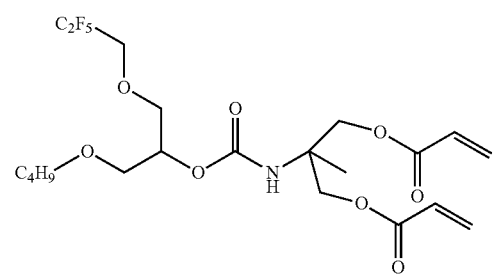
[Chem. 14]
I-31
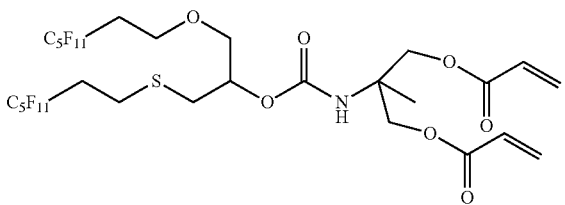
I-32
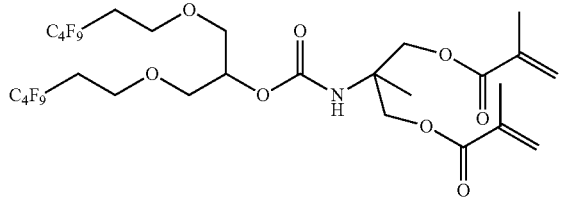

I-33

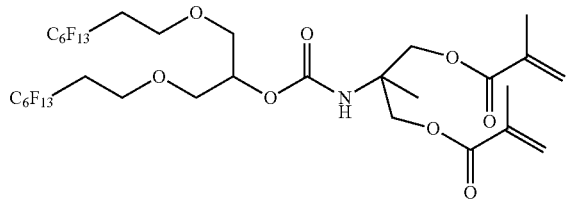

The fluorine-containing urethane (meth)acrylate of the present invention is preferably a fluorine-containing urethane (meth)acrylate in which $R_1$ and $R_2$ are each a $C_nF_{2n+1}CH_2$ group (n is an integer from 2 to 6), a $C_nF_{2n+1}CH_2CH_2$ group (n is an integer from 2 to 6), or a $C_3F_7OCF(CF_3)CH_2$ group. A more preferred one is a fluorine-containing urethane (meth)acrylate in which $R_1$ and $R_2$ are each a $C_6F_{13}CH_2CH_2$ group or a $C_4F_9CH_2CH_2$ group, $R_3$ and $R_4$ are each a hydrogen atom, A is the linking group represented by Structural Formula (A2), and X and Y are each the linking group represented by Structural Formula (a) because it is industrially easily prepared and highly curable and enables formation of a cured coating film having a low refractive index.

In particular, the fluorine-containing urethane (meth)acrylate of the present invention is preferably any of the fluorine-containing urethane (meth)acrylates (I-6) and (I-10) described above.

The fluorine-containing urethane (meth)acrylate of the present invention can be produced through, for example, the reaction of a fluorine-containing alcohol represented by General Formula (II) with an isocyanate di(meth)acrylate represented by General Formula (III).

[Chem. 15]

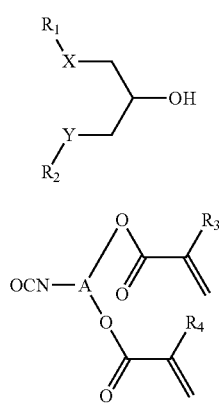

(II)

(III)

(in the formulae, $R_1$ and $R_2$ each independently represent a fluorinated alkyl group in which the number of carbon atoms to which fluorine atoms are directly bonded is from 2 to 6 or a fluorinated alkyl group which has a bond via an oxygen atom and in which the number of carbon atoms to which fluorine atoms are directly bonded is from 2 to 6 in total; $R_3$ and $R_4$ each represent a hydrogen atom or a methyl group; A represents a trivalent linking group represented by any of Structural Formulae (A1) to (A4); and X and Y each independently represent a divalent linking group represented by any of Structural Formulae (a) to (c))

Specific examples of "$R_1$—X—" and "$R_2$—X—" in General Formula (II) include $C_2F_5CH_2O$—, $C_3F_7CH_2O$—, $C_4F_9CH_2O$—, $C_5F_{11}CH_2O$—, $C_6F_{13}CH_2O$—, $C_2F_5CH_2CH_2O$—, $C_3F_7CH_2CH_2O$—, $C_4F_9CH_2CH_2O$—, $C_5F_{11}CH_2CH_2O$—, $C_6F_{13}CH_2CH_2O$—, $C_4F_9CH_2CH_2S$—, $C_6F_{13}CH_2CH_2S$—, $C_3F_7OCF(CF_3)CH_2O$—, $C_4F_9SO_2NC_2H_5$, $C_4F_9SO_2NC_4H_9$, $C_4F_9SO_2NC_6H_{13}$, $C_3F_7OCF(CF_3)CH_2O$—, and $C_3F_7OCF(CF_3)CH_2S$—. "$R_1$—X—" and "$R_2$—X—" may be the same as or different from each other. Such "$R_1$—X—" may be or may not be combined, and "$R_2$—X—" may be or may not be combined as well.

Examples of the fluorine-containing alcohol represented by General Formula (II) include fluorine-containing alcohols having the following structures.

[Chem. 16]

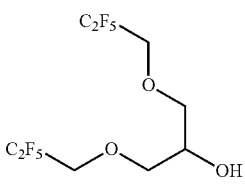

II-1

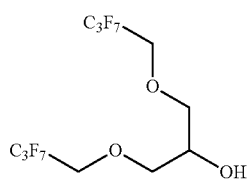

II-2

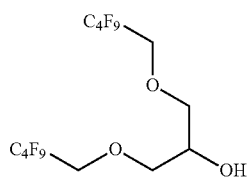

II-3

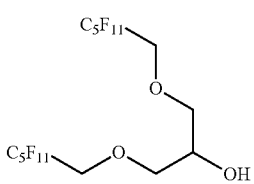

II-4

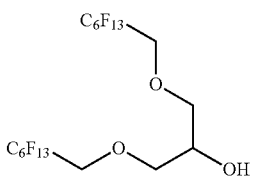

II-5

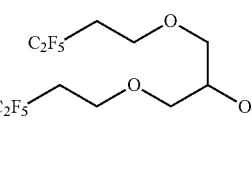

II-6

[Chem. 17]

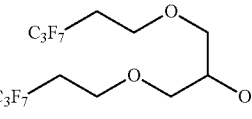

II-7

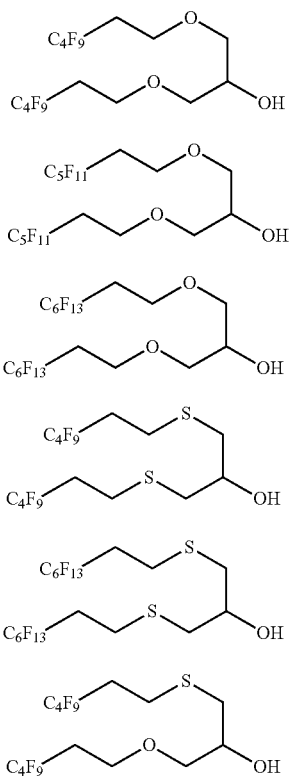

[Chem. 18]

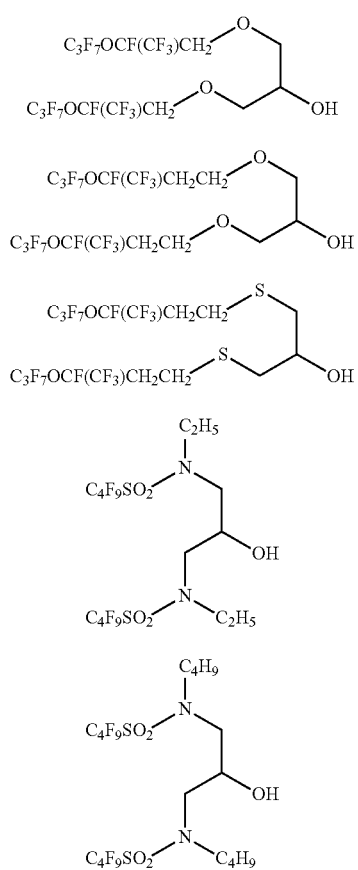

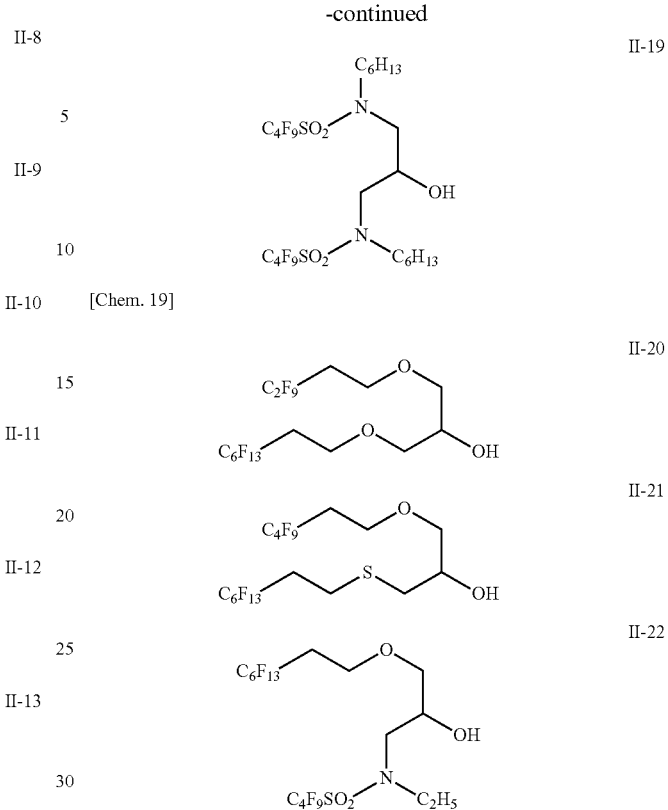

The fluorine-containing alcohol can be prepared by any of techniques, for instance, disclosed in Japanese Unexamined Patent Application Publication Nos. 1-193236, 9-67334, and 2002-3428. In particular, it can be prepared, for example, by the reaction of an epoxy compound having a fluorinated alkyl group with a monoalcohol having a fluorinated alkyl group in the presence of a catalyst selected from the group consisting of alkali metals, alkali metal hydroxides, alkaline earth metal hydroxides, tertiary amines, quaternary amines, and mineral acids.

Examples of the isocyanate di(meth)acrylate represented by General Formula (III) include compounds having the following structures.

[Chem. 20]

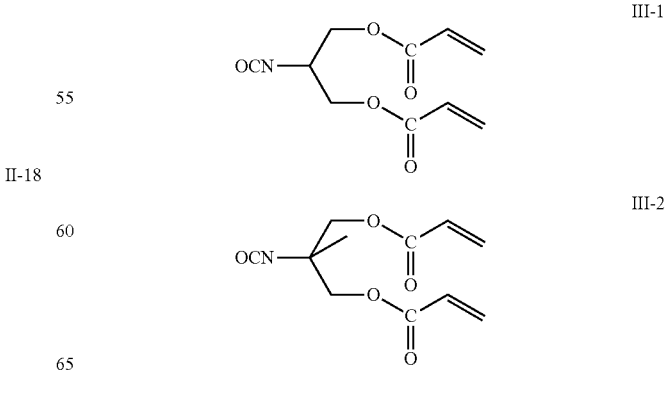

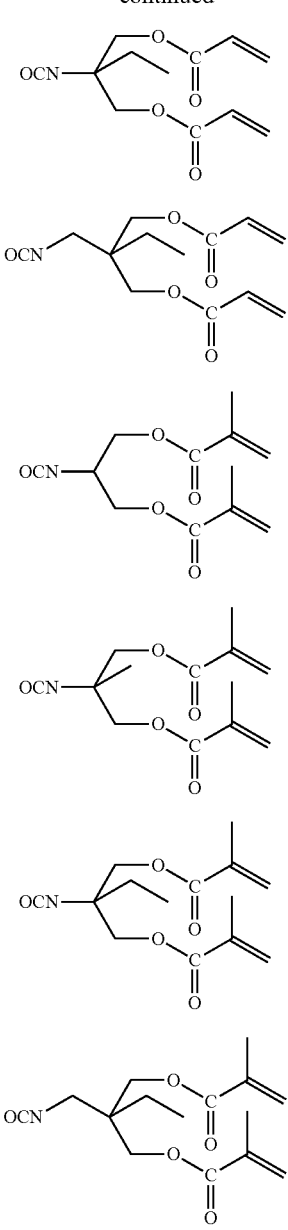

Among such isocyanate di(meth)acrylates (III), the isocyanate di(meth)acrylate (III-2) is preferred because it can be industrially easily prepared.

In the reaction of the fluorine-containing alcohol represented by General Formula (II) with the isocyanate di(meth)acrylate represented by General Formula (III) for production of the urethane (meth)acrylate of the present invention, the isocyanate di(meth)acrylate (III) represented by General Formula (III) is desirably prepared such that the amount thereof is from 0.80 to 1.20 mol relative to 1 mol of the fluorine-containing alcohol represented by General Formula (II), and more desirably from 1.0 to 1.05 mol. In the reaction (urethane reaction), for instance, a tertiary amine, such as triethylamine or benzyldimethylamine, or a tin compound, such as dibutyltin dilaurate, dioctyltin dilaurate, or tin 2-ethylhexanoate, can be used as a catalyst in order to promote the reaction of the secondary hydroxyl group of the fluorine-containing alcohol represented by General Formula (II) with the isocyanate group at the terminal of the isocyanate di(meth)acrylate represented by General Formula (III).

The amount of the catalyst to be added is preferably in the range of 0.001 to 5.0 mass %, more preferably 0.01 to 1.1 mass %, and further preferably 0.02 to 0.2 mass % relative to the amount of the whole reaction mixture. The reaction time is preferably from 1 to 10 hours. The reaction temperature is preferably from 30 to 120° C., and more preferably 60 to 90° C.

In production of the fluorine-containing urethane (meth)acrylate of the present invention in the above-mentioned manner, the reaction can be performed without solvent or with a reaction solvent that is inactive to the isocyanate group, such as acetone, methyl ethyl ketone, toluene, or xylene.

The fluorine-containing urethane (meth)acrylate of the present invention has a low refractive index. In particular, the refractive index of the fluorine-containing urethane (meth)acrylate of the present invention is not more than 1.440, preferably not more than 1.420, and more preferably not more than 1.400. Thus, a curable composition containing the fluorine-containing urethane (meth)acrylate of the present invention [referred to as fluorine-containing urethane (meth)acrylate (I) where appropriate] and having a low refractive index can be provided.

The curable composition of the present invention enables formation of a cured coating film having a low reflectance. It can be therefore suitably used in an antireflective coating for forming an antireflective coating film (the curable composition of the present invention that is used in an antireflective coating is herein referred to as antireflective coating material). The antireflective coating material may further contain a low-refractive-index agent (II), so that the quality thereof can be improved to be more preferred.

The low-refractive-index agent (II) preferably has a refractive index of not more than 1.44, and more preferably not more than 1.40. The low-refractive-index agent (II) may be either inorganic or organic.

Examples of inorganic low-refractive-index agent (II) include fine particles having voids and fine particles of metal fluoride. Examples of the fine particles having voids include fine particles of which the inside has been filled with gas and fine particles having a porous structure that contains gas inside. Specific examples thereof include fine hollow silica particles and fine silica particles having a nanoporous structure. Examples of the fine particles of metal fluoride include fine particles of magnesium fluoride, aluminum fluoride, calcium fluoride, or lithium fluoride.

Among these inorganic low-refractive-index agents, fine hollow silica particles are preferred. These inorganic low-refractive-index agents may be used alone or in combination. The inorganic low-refractive-index agents may be in any form such as crystal, sol, or gel.

The fine hollow silica particles may have any shape including a sphere, a chain, a needle, a plate, a scale, a rod, a fiber, and an amorphous form; however, it is preferably in the form of a sphere or a needle. In the case where the fine silica particles are in the spherical form, the average particle size thereof is preferably in the range of 5 to 100 nm, more preferably 20 to 80 nm, and further preferably 40 to 70 nm. At an average particle size in such a range, the spherical fine particles may give good transparency to a low-refractive-index layer.

Examples of organic low-refractive-index agent (II) include fine particles having voids and fluorine-containing copolymers. The fine particles having voids are preferably polymeric fine hollow particles. Examples of the polymeric fine hollow particles can be, for instance, produced as follows: a mixture of (1) at least one crosslinkable monomer, (2) a polymerization initiator, (3) a polymer of at least one crosslinkable monomer or a copolymer of at least one crosslinkable monomer and at least one monofunctional monomer, and a poorly water-soluble solvent that is less soluble in the materials (1) to (3) is dispersed in an aqueous solution of a dispersion stabilizer for emulsion polymerization. The term "crosslinkable monomer" herein refers to a monomer having two or more polymerizable groups, and the term "monofunctional monomer" herein refers to a monomer having one polymerizable group.

The fluorine-containing copolymer used as the organic low-refractive-index agent is a resin that has a large fluorine atom content and that thus has a low refractive index. Examples of such a fluorine-containing copolymer include copolymers in which vinylidene fluoride and hexafluoropropylene are used as monomeric materials.

The amounts of the monomers as the materials of the fluorine-containing copolymers are as follows: the amount of vinylidene fluoride is preferably from 30 to 90 mass %, more preferably 40 to 80 mass % and further preferably 40 to 70 mass %; and the amount of hexafluoropropylene is from 5 to 50 mass %, more preferably 10 to 50 mass %, and further preferably 15 to 45%. In addition, 0 to 40 mass % of tetrafluoroethylene may be used as another monomer.

The fluorine-containing copolymer can further contain other material monomers; examples thereof include polymerizable monomers having a fluorine atom, such as fluoroethylene, trifluoroethylene, chlorotrifluoroethylene, 1,2-dichloro-1,2-difluoroethylene, 2-bromo-3,3,3-trifluoroethylene, 3-bromo-3,3-difluoropropylene, 3,3,3-trifluoropropylene, 1,1,2-trichloro-3,3,3-trifluoropropylene, and α-trifluoromethacrylic acid. The amount of such other material monomers to be used is preferably not more than 20 mass % relative to the amount of all of the material monomers used in the fluorine-containing copolymer.

The fluorine content in the fluorine-containing copolymer is preferably in the range of 60 to 70 mass %, more preferably 62 to 70 mass %, and further preferably 64 to 68 mass %. At a fluorine content in the fluorine-containing copolymer in such a range, the fluorine-containing copolymer has an excellent solubility in a solvent and is therefore highly adhesive to a variety of substrates, which enables formation of a thin film having a high transparency, a low refractive index, and an excellent mechanical strength.

The number average molecular weight of the fluorine-containing copolymer is preferably in the range of 5,000 to 200,000, and more preferably 10,000 to 100,000 in terms of polystyrene. The molecular weight of the fluorine-containing copolymer in such a range enables production of a resin having a good viscosity and excellent coating properties. The refractive index of the fluorine-containing copolymer itself is preferably not more than 1.44, more preferably not more than 1.42, and further preferably not more than 1.40.

The mass ratio of the fluorine-containing urethane (meth)acrylate (I) to the low-refractive-index agent (II) (I):(II) is preferably from 10:90 to 80:20, more preferably 20:80 to 70:30, and further preferably 30:70 to 60:40 because such a mass ratio enables both reducing the refractive index of a coating film and giving strength thereto.

The antireflective coating composition of the present invention may contain, in addition to the fluorine-containing urethane (meth)acrylate (I), a compound that has a photopolymerizable functional group and that can be subjected to a polymerization or crosslinking reaction by being irradiated with active energy rays such as ultraviolet rays [active-energy-ray-curable compound (III)].

An example of the active-energy-ray-curable compound (III) is an active-energy-ray-curable monomer (III-1). Examples of the monomer (III-1) include ethylene glycol di(meth)acrylate, diethylene glycol di(meth)acrylate, triethylene glycol di(meth)acrylate, polyethylene glycol di(meth)acrylate having a number average molecular weight ranging from 150 to 1000, propylene glycol di(meth)acrylate, dipropylene glycol di(meth)acrylate, tripropylene glycol di(meth)acrylate, polypropylene glycol di(meth)acrylate having a number average molecular weight ranging from 150 to 1000, neopentyl glycol di(meth)acrylate, 1,3-butanediol di(meth)acrylate, 1,4-butanediol di(meth)acrylate, 1,6-hexanediol di(meth)acrylate, hydroxypivalic acid ester neopentyl glycol di(meth)acrylate, bisphenol A di(meth)acrylate, trimethylolpropane tri(meth)acrylate, pentaerythritol tri(meth)acrylate, dipentaerythritol hexa(meth)acrylate, pentaerythritol tetra(meth)acrylate, trimethylolpropane di(meth)acrylate, dipentaerythritol penta(meth)acrylate, and dicyclopentenyl (meth)acrylate; aliphatic alkyl (meth)acrylates such as methyl (meth)acrylate, propyl (meth)acrylate, butyl (meth)acrylate, t-butyl (meth)acrylate, 2-ethylhexyl (meth)acrylate, octyl (meth)acrylate, decyl (meth)acrylate, isodecyl (meth)acrylate, lauryl (meth)acrylate, stearyl (meth)acrylate, and isostearyl (meth)acrylate; and glycerol (meth)acrylate, 2-hydroxyethyl (meth)acrylate, 3-chloro-2-hydroxypropyl (meth)acrylate, glycidyl (meth)acrylate, allyl (meth)acrylate, 2-butoxyethyl (meth)acrylate, 2-(diethylamino)ethyl (meth)acrylate, 2-(dimethylamino)ethyl (meth)acrylate, γ-(meth)acryloxypropyltrimethoxysilane, 2-methoxyethyl (meth)acrylate, methoxydiethylene glycol (meth)acrylate, methoxydipropylene glycol (meth)acrylate, nonylphenoxypolyethylene glycol (meth)acrylate, nonylphenoxypolypropylene glycol (meth)acrylate, phenoxyethyl (meth)acrylate, phenoxydipropylene glycol (meth)acrylate, phenoxypolypropylene glycol (meth)acrylate, polybutadiene (meth)acrylate, polyethylene glycol-polypropylene glycol (meth)acrylate, polyethylene glycol-polybutylene glycol (meth)acrylate, polystyrylethyl (meth)acrylate, benzyl (meth)acrylate, cyclohexyl (meth)acrylate, dicyclopentanyl (meth)acrylate, dicyclopentenyl (meth)acrylate, isobornyl (meth)acrylate, methoxylated cyclodecatriene (meth)acrylate, and phenyl (meth)acrylate.

Among these, polyfunctional (meth)acrylates having a functionality of three or more, such as trimethylolpropane tri(meth)acrylate, pentaerythritol tri(meth)acrylate, dipentaerythritol hexa(meth)acrylate, and pentaerythritol tetra(meth)acrylate, are particularly preferred because they enable production of a cured coating film having a high hardness. Such active-energy-ray-curable monomers (III-1) may be used alone or in combination.

The term "(meth)acrylate" herein refers to any one or both of methacrylate and acrylate. The term "(meth)acryloyl group" herein refers to any one or both of a methacryloyl group and an acryloyl group. The term "(meth)acrylic acid" herein refers to any one or both of a methacrylic acid and an acrylic acid.

Another example of the active-energy-ray-curable compound (III) is an active-energy-ray-curable resin (III-2). Examples of the active-energy-ray-curable resin (III-2) include urethane (meth)acrylate resins other than the fluorine-containing urethane (meth)acrylate, unsaturated polyester resins, epoxy (meth)acrylate resins, polyester (meth)acrylate resins, and acrylic (meth)acrylate resins; in the present invention, urethane (meth)acrylate resins are preferred in view of transparency and low shrinkage.

Examples of the urethane (meth)acrylate resins to be used include resins having a urethane bond and a (meth)acryloyl group and produced through the reaction of an aliphatic polyisocyanate compound or an aromatic polyisocyanate compound with a (meth)acrylate compound having a hydroxyl group.

Examples of the aliphatic polyisocyanate compound include tetramethylene diisocyanate, pentamethylene diisocyanate, hexamethylene diisocyanate, heptamethylene diisocyanate, octamethylene diisocyanate, decamethylene diisocyanate, 2-methyl-1,5-pentane diisocyanate, 3-methyl-1, 5-pentane diisocyanate, dodecamethylene diisocyanate, 2-methylpentamethylene diisocyanate, 2,2,4-trimethylhexamethylene diisocyanate, 2,4,4-trimethylhexamethylene diisocyanate, isophorone diisocyanate, norbornane diisocyanate, hydrogenated diphenylmethane diisocyanate, hydrogenated tolylene diisocyanate, hydrogenated xylylene diisocyanate, hydrogenated tetramethylxylylene diisocyanate, and cyclohexyl diisocyanate. Examples of the aromatic polyisocyanate compound include tolylene diisocyanate, 4,4'-diphenylmethane diisocyanate, xylylene diisocyanate, 1,5-naphthalene diisocyanate, tolidine diisocyanate, and p-phenylene diisocyanate.

Examples of the acrylate compound having a hydroxyl group include 2-hydroxyethyl (meth)acrylate, 2-hydroxypropyl (meth)acrylate, 2-hydroxybutyl (meth)acrylate, and 4-hydroxybutyl (meth)acrylate; dihydric alcohol mono (meth)acrylates such as 1,5-pentanediol mono(meth)acrylate, 1,6-hexanediol mono(meth)acrylate, neopentyl glycol mono(meth)acrylate, and hydroxypivalate neopentyl glycol mono(meth)acrylate; trihydric alcohol mono- or di(meth) acrylates such as trimethylolpropane di(meth)acrylate, ethoxylated trimethylolpropane (meth)acrylate, propoxylated trimethylolpropane di(meth)acrylate, glycerin di(meth) acrylate, and bis(2-(meth)acryloyloxyethyl)hydroxyethylisocyanurate; mono- or di(meth)acrylates having a hydroxyl group and provided by modifying some of alcoholic hydroxyl groups of the foregoing with ε-caprolactone; compounds having a monofunctional hydroxyl group and tri- or higher-functional (meth)acryloyl group, such as pentaerythritol tri(meth)acrylate, ditrimethylolpropane tri(meth)acrylate, and dipentaerythritol penta(meth)acrylate; polyfunctional (meth)acrylates having a hydroxyl group and provided by modifying the compounds with ε-caprolactone; (meth) acrylate compounds having an oxyalkylene chain, such as dipropylene glycol mono(meth)acrylate, diethylene glycol mono(meth)acrylate, polypropylene glycol mono(meth) acrylate, and polyethylene glycol mono(meth)acrylate; (meth)acrylate compounds having block oxyalkylene chains, such as polyethylene glycol-polypropylene glycol mono(meth)acrylate and polyoxybutylene-polyoxypropylene mono(meth)acrylate; and (meth)acrylate compounds having random oxyalkylene chains, such as poly(ethylene glycol-tetramethylene glycol) mono(meth)acrylate and poly (propylene glycol-tetramethylene glycol) mono(meth)acrylate.

The above-mentioned reaction of an aliphatic polyisocyanate compound or an aromatic polyisocyanate compound with an acrylate compound having a hydroxyl group can be performed by a routine procedure in the presence of a urethanation catalyst. Specific examples of a usable urethanation catalyst include amines such as pyridine, pyrrole, triethylamine, diethylamine, and dibutylamine; phosphines such as triphenylphosphine and triethylphosphine; organic tin compounds such as dibutyl tin dilaurate, octyl tin trilaurate, octyl tin diacetate, dibutyl tin diacetate, and tin octylate; and organic metal compounds such as zinc octylate.

Among the urethane acrylate resins, resins obtained through a reaction of an aliphatic polyisocyanate compound with a (meth)acrylate compound having a hydroxyl group are particularly preferred because they enable a cured coating film to have a high transparency and are highly sensitive to active energy rays and thus highly curable.

The unsaturated polyester resin is a curable resin obtained through polycondensation of an α,β-unsaturated dibasic acid, an acid anhydride thereof, an aromatic saturated dibasic acid, or an acid anhydride thereof with a glycol. Examples of the α,β-unsaturated dibasic acid or the acid anhydride thereof include maleic acid, maleic anhydride, fumaric acid, itaconic acid, citraconic acid, chloromaleic acid, and esters of the foregoing. Examples of the aromatic saturated dibasic acid or the acid anhydride thereof include phthalic acid, phthalic anhydride, isophthalic acid, terephthalic acid, nitrophthalic acid, tetrahydrophthalic anhydride, endomethylene tetrahydrophthalic anhydride, halogenated phthalic anhydrides, and esters of the foregoing. Examples of an aliphatic or alicyclic saturated dibasic acid include oxalic acid, malonic acid, succinic acid, adipic acid, sebacic acid, azelaic acid, glutaric acid, hexahydrophthalic anhydride, and esters of the foregoing. Examples of the glycol include ethylene glycol, propylene glycol, diethylene glycol, dipropylene glycol, 1,3-butanediol, 1,4-butanediol, 2-methylpropane-1,3-diol, neopentyl glycol, triethylene glycol, tetraethylene glycol, 1,5-pentanediol, 1,6-hexanediol, bisphenol A, hydrogenated bisphenol A, ethylene glycol carbonate, and 2,2-di-(4-hydroxypropoxydiphenyl)propane; and an oxide such as ethylene oxide or propylene oxide may be similarly used.

Examples of an epoxy vinyl ester resin include resins obtained through the reaction of (meth)acrylic acid with an epoxy group of an epoxy resin such as a bisphenol A epoxy resin, a bisphenol F epoxy resin, a phenol-novolac epoxy resin, or a cresol-novolac epoxy resin. These active-energy-ray-curable resins (III-2) may be used alone or in combination.

The active-energy-ray-curable monomer (III-1) and the active-energy-ray-curable resin (III-2) may be used alone or in combination.

The amount of the active-energy-ray-curable compound (III) is, for example, preferably not more than 100 parts by mass, and more preferably not more than 50 parts by mass relative to 100 parts by mass of the fluorine-containing urethane (meth)acrylate (I).

In the case where the antireflective coating composition of the present invention is cured by being irradiated with active energy rays such as ultraviolet rays, a polymerization initiator (IV) is added to the antireflective coating composition of the present invention. Examples of the polymerization initiator (IV) include benzophenone, acetophenone, benzoin, benzoin ethyl ether, benzoin isobutyl ether, benzyl methyl ketal, azobisisobutyronitrile, 1-hydroxycyclohexyl phenyl ketone, 2-hydroxy-2-methyl-1-phenyl-1-one, 1-(4'-isopropylphenyl)-2-hydroxy-2-methylpropane-1-one, 1-(4'-dodecylphenyl)-2-hydroxy-2-methylpropane-1-one, 3,3',4, 4'-tetra(t-butylperoxycarbonyl)benzophenone, 4,4"-diethylisophthalophene, 2,2-dimethoxy-1,2-diphenylethane-1-one, benzoin isopropyl ether, thioxanthone, 2-chlorothioxanthone, 2-methylthioxanthone, 2-isopropylthioxanthone, 2-methyl-1[4-(methylthio)phenyl]-2-morpholinopropane-1-one, 2-benzyl-2-dimethylamino-1-(4-morpholinophenyl)-butanone-1, bis(2,6-dimethoxybenzoyl)-2,4,4-trimethyl-pentylphosphine oxide, bis(2,4,6,-trimethylbenzoyl)-phenylphosphine oxide, and 2,4,6-trimethylbenzoyl diphenylphosphine oxide. These polymerization initiators may be used alone or in combination.

Furthermore, a photosensitizer such as an amine compound or a phosphorus compound may be optionally added to promote photopolymerization.

The amount of the polymerization initiator (IV) is preferably in the range of 0.01 to 15 parts by mass, and more preferably 0.3 to 7 parts by mass relative to 100 parts by mass of the total of the fluorine-containing urethane (meth) acrylate (I), the low-refractive-index agent (II), and the active-energy-ray-curable compound (III) optionally added.

The antireflective coating composition of the present invention may further contain an additive such as an organic solvent, a polymerization inhibitor, an antistatic agent, a defoaming agent, a viscosity modifier, a light stabilizer, a thermal stabilizer, or an antioxidant on the basis of the intended purpose such as application or properties provided that the effect of the present invention is not impaired.

In order to give application suitability to the antireflective coating composition of the present invention, an organic solvent may be used to adjust the viscosity. Examples of a usable organic solvent include acetate solvents such as propylene glycol monomethyl ether acetate and propylene glycol monoethyl ether acetate; propionate solvents such as ethoxypropionate; aromatic solvents such as toluene, xylene, and methoxybenzene; ether solvents such as butyl cellosolve, propylene glycol monomethyl ether, diethylene glycol ethyl ether, and diethylene glycol dimethyl ether; ketone solvents such as methyl ethyl ketone, methyl isobutyl ketone, and cyclohexanone; aliphatic hydrocarbon solvents such as hexane; nitrogen compound solvents such as N,N-dimethylformamide, γ-butyrolactam, and N-methyl-2-pyrrolidone; lactone solvents such as γ-butyrolactone; and carbamate. These solvents may be used alone or in combination.

The amount of the organic solvent to be used is preferably in the range of 4 to 200 times the total mass of the fluorine-containing urethane (meth)acrylate (I), the low-refractive-index agent (II), and the active-energy-ray-curable compound (III) to be optionally added, on the basis of application and the intended thickness and viscosity.

Examples of active energy rays used for curing the antireflective coating composition of the present invention include active energy rays such as light, electron beams, and radiations. Specific examples of an energy source or a curing device include germicidal lamps, fluorescent lamps for ultraviolet rays, carbon arc lamps, xenon lamps, high pressure mercury lamps used for a copy, medium pressure mercury lamps, high pressure mercury lamps, ultra-high pressure mercury lamps, electrodeless lamps, metal halide lamps, ultraviolet rays of which the light source is, for instance, natural light, and electron beams provided by a scanning- or curtain-type electron beam accelerator. In the case where electron beams are used for the curing, the polymerization initiator (IV) does not need to be added to the antireflective coating composition of the present invention.

Among these active energy rays, ultraviolet rays are particularly preferred. Radiating the active energy rays in an atmosphere of an inert gas such as nitrogen gas is preferred because it enhances the surface curability of the coating film. Furthermore, heat may be optionally used in combination as an energy source; the curing with active energy rays is performed, and then heat treatment may be conducted.

Examples of a technique for applying the antireflective coating composition of the present invention include coating techniques involving use of a gravure coater, a roll coater, a comma coater, a knife coater, a curtain coater, a shower coater, a spin coater, a slit coater, dipping, screen printing, a spray, an applicator, or a bar coater.

The antireflective film of the present invention includes a cured coating film of the antireflective coating composition of the present invention. In particular, the antireflective film of the present invention can be formed through, for example, the following process.

(1) A hard coat material is applied to a substrate and then cured to form a hard coat layer.

(2) The antireflective coating composition of the present invention is applied to the hard coat layer and then cured to form a coating film of a low-refractive-index layer. This low-refractive-index layer is the outermost layer of the antireflective film.

An intermediate-refractive-index layer and/or a high-refractive-index layer may be provided between the hard coat layer and the low-refractive-index layer.

Any hard coat material can be used provided that it enables formation of a cured coating film having a relatively high surface hardness; it is preferably a combination of the active-energy-ray-curable monomer (III-1) and the active-energy-ray-curable resin (III-2) that have been described above as examples of the active-energy-ray-curable compound (III).

The thickness of the hard coat layer is preferably in the range of 0.1 to 100 μm, more preferably 1 to 30 μm, and further preferably 3 to 15 μm. The hard coat layer having a thickness in such a range has an enhanced adhesion to the substrate and enables an improvement in the surface hardness of the antireflective film. The hard coat layer may have any refractive index; in the case where its refractive index is high, a good antireflection effect can be produced without the above-mentioned intermediate-refractive-index layer and high-refractive-index layer being provided.

The thickness of the low-refractive-index layer, which is formed by applying and curing the antireflective coating composition of the present invention, is preferably in the range of 50 to 300 nm, more preferably 50 to 150 nm, and further preferably 80 to 120 nm. The thickness of the low-refractive-index layer in such a range can enhance an antireflection effect. The refractive index of the low-refractive-index layer is preferably in the range of 1.20 to 1.45, and more preferably 1.23 to 1.42. The refractive index of the low-refractive-index layer in such a range can enhance an antireflection effect.

The thickness of the intermediate-refractive-index layer or high-refractive-index layer is preferably in the range of 10 to 300 nm, and more preferably 30 to 200 nm. The refractive index of the intermediate-refractive-index layer or high-refractive-index layer is determined on the basis of the refractive indices of the overlying low-refractive-index layer and underlying hard coat layer and can be appropriately determined to be in the range of 1.40 to 2.00.

Examples of the materials for forming the intermediate-refractive-index layer or the high-refractive-index layer include resins that can be cured by being heated or irradiated with ultraviolet rays or electron beams, such as epoxy resins, phenolic resins, melamine resins, alkyd resins, cyanate resins, acrylic resins, polyester resins, urethane resins, and siloxane resins. These resins may be used alone or in combination. It is preferred that these resins be mixed with inorganic fine particles having a high refractive index.

The inorganic fine particles having a high refractive index preferably have a refractive index ranging from 1.65 to 2.00. Examples thereof include zinc oxide having a refractive index of 1.90, titania having a refractive index ranging from 2.3 to 2.7, ceria having a refractive index of 1.95, tin-doped indium oxide having a refractive index ranging from 1.95 to 2.00, antimony-doped tin oxide having a refractive index ranging from 1.75 to 1.85, yttria having a refractive index of 1.87, and zirconia having a refractive index of 2.10. These inorganic fine particles having a high refractive index may be used alone or in combination.

A technique for forming the intermediate-refractive-index layer or the high-refractive-index layer is the same as that used for applying the antireflective coating composition of the present invention, which can enhance productivity. Hence, in the case where the antireflective coating composition of the present invention is cured by being irradiated with ultraviolet rays, it is preferred that a ultraviolet curable composition be used to form the intermediate-refractive-index layer or the high-refractive-index layer.

Examples of the substrate used for forming the antireflective film of the present invention includes polyester films such as polyethylene terephthalate, polybutylene terephthalate, and polyethylene naphthalate; polyolefin films such as polypropylene, polyethylene, and polymethyl pentene-1; cellulose films such as triacetylcellulose (TAC); and polystyrene films, polyamide films, polycarbonate films, norbornene resin films (e.g., "ZEONOR" manufactured by Zeon Corporation), modified norbornene resin films (e.g., "ARTON" manufactured by JSR Corporation), cyclic olefin copolymer films (e.g., "APEL" manufactured by Mitsui Chemicals, Inc.), and acrylic films such as polymethyl methacrylate (PMMA). Two or more of these films may be attached to each other. The films may be in the form of a sheet. The thickness of the film substrate is preferably from 20 to 500 μm.

The reflectance of the antireflective film of the present invention is preferably not more than 2.0%, more preferably not more than 1.5%, and further preferably not more than 1.0%.

The antireflective film of the present invention can be used not only in liquid crystal displays but also in a variety of image display apparatuses. Specific examples of image display apparatuses to which the antireflective film of the present invention can be applied include a plasma display panel (PDP), a cathode-ray tube (CRT) display apparatus, an electroluminescence display, a rear projection display, and a vacuum fluorescent display (VFD).

EXAMPLES

The present invention will now be described further in detail with reference to specific examples. The terms "part" and "%" are herein on a mass basis unless otherwise specified. A fluorine-containing urethane (meth)acrylate to be produced was subjected IR spectroscopy, $^{13}$C-NMR spectroscopy, $^{1}$H-NMR spectroscopy, $^{19}$F-NMR spectroscopy, and GPC under the following conditions.

[Conditions of IR Spectroscopy]
Equipment: "FT/IR-6100" manufactured by JASCO Corporation
Measuring Technique: KBr technique
[Conditions of $^{13}$C-NMR Spectroscopy, $^{1}$H-NMR Spectroscopy, and $^{19}$F-NMR Spectroscopy]
Equipment: "JNM-ECA500" manufactured by JEOL Ltd.
Solvent: Deuterated chloroform
[Conditions of GPC]
Measuring Equipment: "HLC-8220 GPC" manufactured by TOSOH CORPORATION
Column: Guard Column "HHR-H" manufactured by TOSOH CORPORATION (6.0 mm I.D.×4 cm)+"TSK-GEL GMHHR-N" manufactured by TOSOH CORPORATION (7.8 mm I.D.×30 cm)+"TSK-GEL GMHHR-N" manufactured by TOSOH CORPORATION (7.8 mm I.D.×30 cm)+"TSK-GEL GMHHR-N" manufactured by TOSOH CORPORATION (7.8 mm I.D.×30 cm)+"TSK-GEL GMHHR-N" manufactured by TOSOH CORPORATION (7.8 mm I.D.×30 cm)

Detector: ELSD ("ELSD2000" manufactured by Alltech Corporation)
Data Processing: "GPC-8020 model II data analysis version 4.30" manufactured by TOSOH CORPORATION
Measurement Conditions: Column Temperature 40° C.
Eluent tetrahydrofuran (THF)
Flow rate 1.0 ml/min
Sample: 1.0 mass % of tetrahydrofuran solution in terms of the resin solid content was filtered through a microfilter (5 μl)
Standard Sample: the following monodisperse polystyrenes having known molecular weights were used in accordance with the measurement manual of "GPC-8020 model II data analysis version 4.30"
(Monodisperse Polystyrene)
"A-500" manufactured by TOSOH CORPORATION
"A-1000" manufactured by TOSOH CORPORATION
"A-2500" manufactured by TOSOH CORPORATION
"A-5000" manufactured by TOSOH CORPORATION
"F-1" manufactured by TOSOH CORPORATION
"F-2" manufactured by TOSOH CORPORATION
"F-4" manufactured by TOSOH CORPORATION
"F-10" manufactured by TOSOH CORPORATION
"F-20" manufactured by TOSOH CORPORATION
"F-40" manufactured by TOSOH CORPORATION
"F-80" manufactured by TOSOH CORPORATION
"F-128" manufactured by TOSOH CORPORATION
"F-288" manufactured by TOSOH CORPORATION
"F-550" manufactured by TOSOH CORPORATION Example 1 [Fluorine-containing Urethane (Meth)acrylate of Present Invention]

Figure 2:
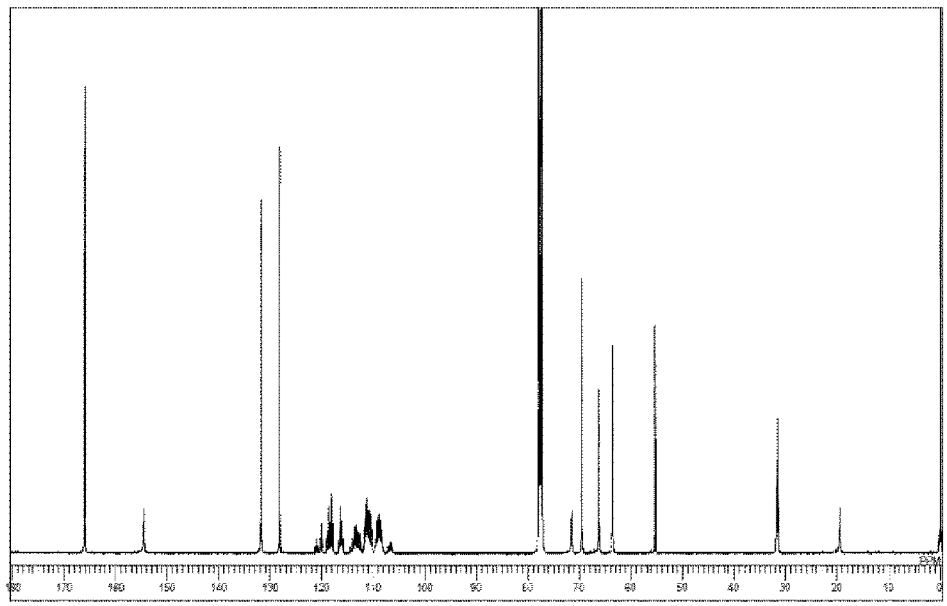
FIG. 2 is a chart illustrating the $^{13}$C-NMR spectrum of the fluorine-containing urethane (meth)acrylate (1) obtained in Example 1.
Figure 3:
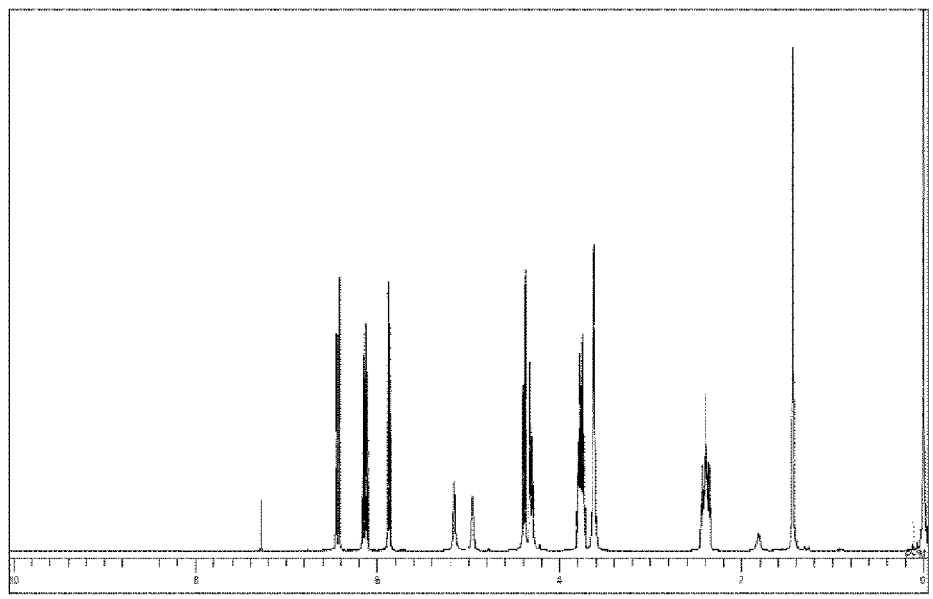
FIG. 3 is a chart illustrating the $^{1}$H-NMR spectrum of the fluorine-containing urethane (meth)acrylate (1) obtained in Example 1.
Figure 4:
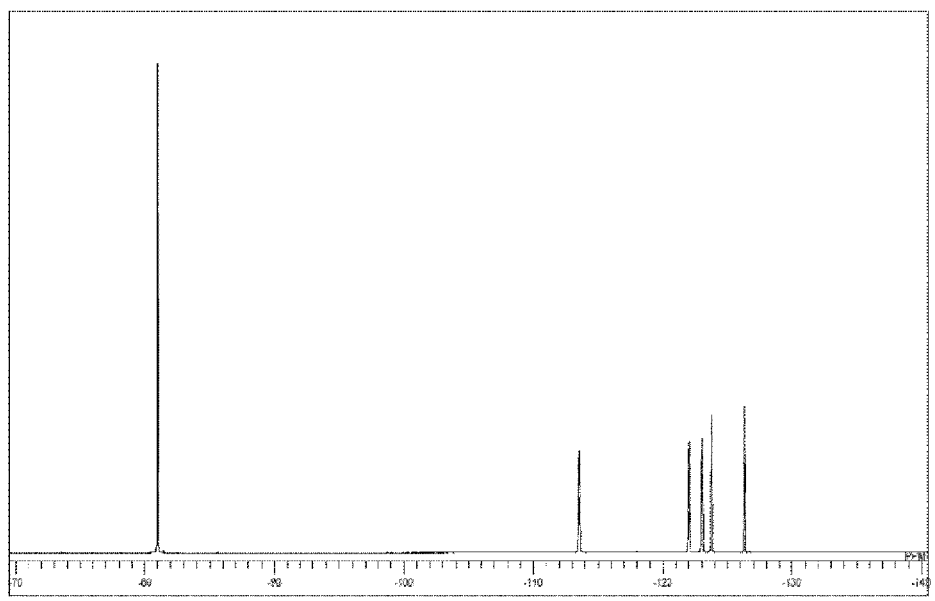
FIG. 4 is a chart illustrating the $^{19}$F-NMR spectrum of the fluorine-containing urethane (meth)acrylate (1) obtained in Example 1.
Figure 5:
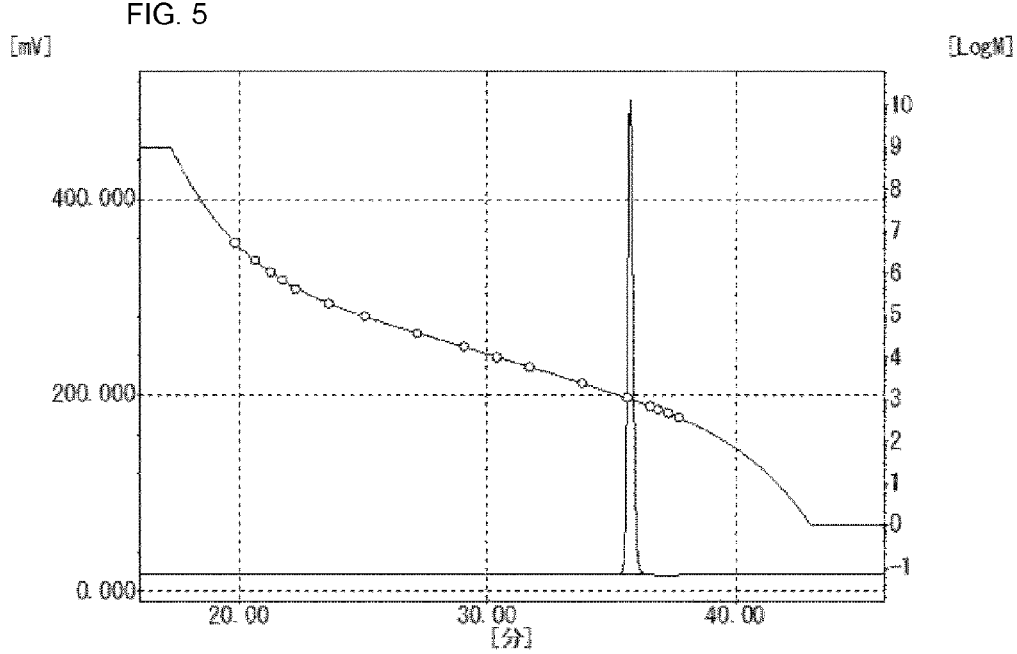
FIG. 5 is a chart illustrating the result of GPC for the fluorine-containing urethane (meth)acrylate (1) obtained in Example 1.

Into a glass flask having a stirrer, a thermometer, a cooling pipe, and a dropping unit, 151.5 g of 1,3-bis(3,3,4,4,5,5,6,6,7,7,8,8,8-tridecafluorooctyloxy)-2-propanol, 0.02 g of p-methoxyphenol, and 0.3 g of tin 2-ethylhexanoate were put; and the temperature was increased to 60° C. while the content was stirred under the flow of dry air. Then, 48.5 g of 1,1-bis(acryloyloxymethyl)ethyl isocyanate was placed in the dropping unit and dropped over an hour while the internal temperature of the flask was maintained at 60° C. After the dropping, the resulting product was stirred at 60° C. for 15 minutes and subsequently at 90° C. for 9 hours to perform a reaction. The resulting product was subjected to IR spectroscopy, and the result of the IR spectroscopy showed loss of the isocyanate group; then, the product was filtered through a filter to obtain 200 g of a fluorine-containing urethane acrylate (I-1) of the present invention. The fluorine-containing urethane acrylate (I-1) was analyzed by GPC, and the result of the analysis showed that the number average molecular weight was 1,010 and that the weight average molecular weight was 1,012. The refractive index thereof was measured at 25° C., and it was 1.383. The fluorine content was calculated from the compositions of the materials, and it was 47.7 mass %. FIG. 1 is a chart illustrating the IR spectrum of the fluorine-containing urethane acrylate (I-1), FIG. 2 is a chart illustrating the $^{13}$C-NMR spectrum thereof, FIG. 3 is a chart illustrating the $^{1}$H-NMR spectrum thereof, FIG. 4 is a chart illustrating the 19F-NMR spectrum thereof, and FIG. 5 is a chart illustrating the result of the GPC therefor.

Example 2 (Same as Above)

Into a glass flask having a stirrer, a thermometer, a cooling pipe, and a dropping unit, 139.9 g of 1,3-bis(3,3,4,4,5,5,6,6,6-nonafluorohexyloxy)-2-propanol, 0.02 g of p-methoxyphenol, and 0.3 g of tin 2-ethylhexanoate were put; and the temperature was increased to 60° C. while the content was stirred under the flow of dry air. Then, 60.1 g of 1,1-bis (acryloyloxymethyl)ethyl isocyanate was placed in the dropping unit and dropped over an hour while the internal temperature of the flask was maintained at 60° C. After the dropping, the product was stirred at 60° C. for 15 minutes and subsequently at 90° C. for 9 hours to perform a reaction. The resulting product was subjected to IR spectroscopy, and the result of the IR spectroscopy showed loss of the isocyanate group; then, the product was filtered through a filter to obtain 200 g of a fluorine-containing urethane acrylate (I-2) of the present invention. The fluorine-containing urethane acrylate (I-2) was analyzed by GPC, and the result of the analysis showed that the number average molecular weight was 714 and that the weight average molecular weight was 716. The refractive index thereof was measured at 25° C., and it was 1.399. The fluorine content was calculated from the compositions of the materials, and it was 41.0 mass %.

Example 3 (Same as Above)

Into a glass flask having a stirrer, a thermometer, a cooling pipe, and a dropping unit, 121.9 g of 1,3-bis(3,3,4,4,4-pentafluorobutyloxy)-2-propanol, 0.02 g of p-methoxyphenol, and 0.3 g of tin 2-ethylhexanoate were put; and the temperature was increased to 60° C. while the content was stirred under the flow of dry air. Then, 78.1 g of 1,1-bis (acryloyloxymethyl)ethyl isocyanate was placed in the dropping unit and dropped over an hour while the internal temperature of the flask was maintained at 60° C. After the dropping, the product was stirred at 60° C. for 15 minutes and subsequently at 90° C. for 9 hours to perform a reaction. The resulting product was subjected to IR spectroscopy, and the result of the IR spectroscopy showed loss of the isocyanate group; then, the product was filtered through a filter to obtain 200 g of a fluorine-containing urethane acrylate (I-3) of the present invention. The fluorine-containing urethane acrylate (I-3) was analyzed by GPC, and the result of the analysis showed that the number average molecular weight was 615 and that the weight average molecular weight was 617. The refractive index thereof was measured at 25° C., and it was 1.425. The fluorine content was calculated from the compositions of the materials, and it was 30.2 mass %.

Comparative Example 1 [Comparative Fluorine-Containing Urethane (Meth)acrylate]

Into a glass flask having a stirrer, a thermometer, a cooling pipe, and a dropping unit, 168.2 g of 1,3-bis(3,3,4,4,5,5,6,6,7,7,8,8,8-tridecafluorooctyloxy)-2-propanol, 0.02 g of p-methoxyphenol, and 0.3 g of tin 2-ethylhexanoate were put; and the temperature was increased to 60° C. while the content was stirred under the flow of dry air. Then, 31.8 g of acryloyloxyethyl isocyanate was placed in the dropping unit and dropped over an hour while the internal temperature of the flask was maintained at 60° C. After the dropping, the product was stirred at 60° C. for 15 minutes and subsequently at 90° C. for 9 hours to perform a reaction. The resulting product was subjected to IR spectroscopy, and the result of the IR spectroscopy showed loss of the isocyanate group; then, the product was filtered through a filter to obtain 200 g of a comparative fluorine-containing urethane acrylate (I'-1). The comparative fluorine-containing urethane acrylate (I'-1) was analyzed by GPC, and the result of the analysis showed that the number average molecular weight was 913 and that the weight average molecular weight was 915. The refractive index thereof was measured at 25° C., and it was 1.369. The fluorine content was calculated from the compositions of the materials, and it was 53.0 mass %.

Comparative Example 2 [Same as Above]

Into a glass flask having a stirrer, a thermometer, a cooling pipe, and a dropping unit, 106.2 g of 1,3-bis(3,3,3-trifluoropropyloxy)-2-propanol, 0.02 g of p-methoxyphenol, and 0.3 g of tin 2-ethylhexanoate were put; and the temperature was increased to 60° C. while the content was stirred under the flow of dry air. Then, 93.8 g of 1,1-bis(acryloyloxymethyl)ethyl isocyanate was placed in the dropping unit and dropped over an hour while the internal temperature of the flask was maintained at 60° C. After the dropping, the product was stirred at 60° C. for 15 minutes and subsequently at 90° C. for 9 hours to perform a reaction. The resulting product was subjected to IR spectroscopy, and the result of the IR spectroscopy showed loss of the isocyanate group; then, the product was filtered through a filter to obtain 200 g of a fluorine-containing urethane acrylate (I'-2) of the present invention. The fluorine-containing urethane acrylate (I'-2) was analyzed by GPC, and the result of the analysis showed that the number average molecular weight was 516 and that the weight average molecular weight was 518. The refractive index thereof was measured at 25° C., and it was 1.446. The fluorine content was calculated from the compositions of the materials, and it was 21.3 mass %.

Example 4 [Antireflective Coating Composition and Antireflective Film]

<Preparation of Antireflective Coating Composition>

An antireflective coating composition (1) of the present invention was prepared by mixing and dissolving 12.2 parts of a dispersion liquid of methyl isobutyl ketone that contained 20% of fine hollow silica particles (average particle size: 60 nm), 2.0 parts of the fluorine-containing urethane acrylate (I-1), 0.1 part of 2-hydroxy-1-{4-[4-(2-hydroxy-2-methyl-propionyl)-benzyl]-phenyl}-2-methyl-propane-1-one ("Irgacure 127" manufactured by Ciba Japan K.K.) that served as a photopolymerization initiator, and 85.7 parts of methyl isobutyl ketone that served as a solvent. The antireflective coating composition (1) was used to produce an antireflective film as follows.

<Production of Antireflective Film>

A coating composition used for forming a hard coat layer was prepared by mixing and dissolving 50 parts of pentafunctional non-yellowing urethane acrylate; 50 parts of dipentaerythritol hexaacrylate; 25 parts of butyl acetate; 5 parts of 1-hydroxycyclohexyl phenyl ketone ("Irgacure 184" manufactured by Ciba Specialty Chemicals) that served as a photopolymerization initiator; and 54 parts of toluene, 28 parts of 2-propanol, 28 parts of ethyl acetate, and 28 parts of propylene glycol monomethyl ether that served as solvents. This coating composition used for forming a hard coat layer was applied to a TAC film having a thickness of 80 μm with a bar coater No. 13, left in a dryer at 60° C. for 5 minutes to volatilize the solvents, and then cured with an ultraviolet curing apparatus (in a nitrogen atmosphere, use of a high pressure mercury lamp, radiation dose of ultraviolet rays: 2 kJ/m2), thereby producing a hard coat film of which a hard coat layer having a thickness of 10 μm was disposed on the one side.

The antireflective coating composition (1) was applied onto the hard coat layer of the hard coat film with a bar coater No. 2 such that the amount of the antireflective coating composition (1) was 2 g/m2, left in a dryer at 60° C. for 5 minutes to volatilize the solvent, and then cured with an ultraviolet curing apparatus (in a nitrogen atmosphere, use of high pressure mercury lamp, radiation dose of ultraviolet rays: 2 kJ/m$^2$), thereby producing an antireflective film (1) in which an antireflective layer having a thickness of 0.1 μm was disposed on the hard coat layer having a thickness of 10 μm.

The surface of the cured coating film of the antireflective coating composition at the top of the antireflective film (1) was subjected to evaluation of excoriation resistance. In addition, the reflectance of the antireflective film (1) was measured. The evaluation of excoriation resistance and the measurement of reflectance were as follows. Table 1 sows results of the evaluation and measurement.

<Evaluation of Excoriation Resistance>

A both-way wear test was performed 10 times with a both-way wear tester TriboGear HEIDON Type 30S (manufactured by Shinto Scientific Co., Ltd.) of which a Bonstar No. 0000 (manufactured by NIHON STEEL WOOL Co., Ltd.) was attached to the 27-mm-diameter circular jig (load: 300 g/cm2). The number of scars generated on the surface of the coating film was counted after the test to evaluate the excoriation resistance on the basis of the following criteria.

Good: Number of scars was less than 10
Acceptable: Number of scars was 10 or more but less than 50
Bad: Number of scars was 50 or more <Measurement of Reflectance>

A spectrophotometer ("UV-3100PC" manufactured by SHIMADZU CORPORATION) having a five-degree specular-reflection-measuring device was used to measure reflectance. The reflectance to be measured was the minimum value (smallest reflectance) near a wavelength of 550 nm.

Examples 5 and 6 (Same as Above)

Except that 2.0 parts of the fluorine-containing urethane acrylates (I-2) and (I-3) were used in place of 2.0 parts of the fluorine-containing urethane acrylate (I-1), antireflective coating compositions (2) and (3) were produced as in Example 1, respectively. Then, antireflective films (2) and (3) were produced as in Example 1. As in Example 1, the surfaces of the cured coating films of the antireflective coating compositions at the tops of the antireflective films (2) and (3) were subjected to the evaluation of excoriation resistance, and the antireflective films (2) and (3) were subjected to the measurement of reflectance. Table 1 shows results of the evaluation and measurement.

Comparative Examples 3 and 4 [Comparative Antireflective Coating Composition and Antireflective Film]

Except that 2.0 parts of the comparative fluorine-containing urethane acrylates (I'-1) and (I'-2) were used in place of 2.0 parts of the fluorine-containing urethane acrylate (I-1), comparative antireflective coating compositions (1') and (2') were produced as in Example 1, respectively. Then, comparative antireflective films (1') and (2') were produced as in Example 1. As in Example 1, the surfaces of the cured coating films of the antireflective coating compositions at the tops of the comparative antireflective films (1') and (2') were subjected to the evaluation of excoriation resistance, and the comparative antireflective films (1') and (2') were subjected to the measurement of reflectance. Table 2 shows results of the evaluation and measurement.

TABLE 1

|  | Example 4 | Example 5 | Example 6 |
| --- | --- | --- | --- |
| Antireflective film | 1 | 2 | 3 |
| Fluorine-containing urethane (meth)acrylate | (I-1) | (I-2) | (I-3) |
| Excoriation resistance | Good | Good | Good |
| Reflectance (%) | 0.4 | 0.6 | 0.8 |

TABLE 2

|  | Comparative Example 3 | Comparative Example 4 |
| --- | --- | --- |
| Antireflective film | 1' | 2' |
| Fluorine-containing urethane (meth)acrylate | (I'-1) | (I'-2) |
| Excoriation resistance | Bad | Good |
| Reflectance (%) | 0.4 | 1.0 |

The invention claimed is:

1. A fluorine-containing urethane (meth)acrylate represented by General Formula (I) and having a fluorine atom content ranging from 25 to 60 mass %

[Chem. 1]

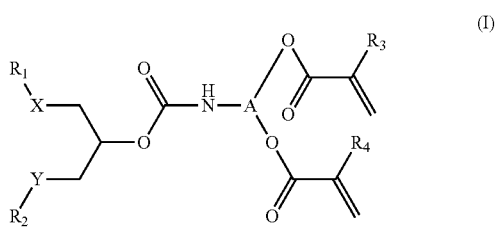

(I)

where $R_1$ and $R_2$ each independently represent a fluorinated alkyl group in which the number of carbon atoms to which fluorine atoms are directly bonded is from 2 to 6 or a fluorinated alkyl group which has a bond via an oxygen atom and in which the number of carbon atoms to which fluorine atoms are directly bonded is from 2 to 6 in total; $R_3$ and $R_4$ each represent a hydrogen atom or a methyl group; A represents a trivalent linking group represented by any of Structural Formulae (A1) to (A4); and X and Y each independently represent a divalent linking group represented by any of Structural Formulae (a) to (c)

[Chem. 2]

(A1)

-continued

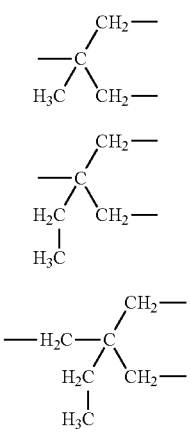

(A2)

(A3)

(A4)

[Chem. 3]

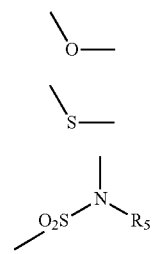

(a)

(b)

(c)

in Structural Formula (c), R5 represents an alkyl group having 1 to 6 carbon atoms.

2. The fluorine-containing urethane (meth)acrylate according to claim 1, wherein the fluorine atom content is from 35 to 60 mass %.

3. The fluorine-containing urethane (meth)acrylate according to claim 1, wherein $R_1$ and $R_2$ are each a $C_nF_{21}CH_2$ group and n is an integer from 2 to 6, a $C_nF2_{n+1}CH_2CH_2$ group and n is an integer from 2 to 6, or a $C_3F_7OCF(CF_3)CH_2$ group.

4. The fluorine-containing urethane (meth)acrylate according to claim 1, wherein $R_1$ and $R_2$ are each a $C_6F_{13}CH_2CH_2$ group or a $C_4F_9CH_2CH_2$ group, $R_3$ and $R_4$ are each a hydrogen atom, A is a linking group represented by Structural Formula (A2), and X and Y are each a linking group represented by Structural Formula (a).

5. A curable composition comprising the fluorine-containing urethane (meth)acrylate (I) according to claim 1.

6. The curable composition according to claim 5, further comprising a low-refractive-index agent (II).

7. The curable composition according to claim 6, wherein the low-refractive-index agent (II) is fine hollow silica particles.

8. An antireflective film comprising a cured coating film of the curable composition according to claim 5.

9. The antireflective film according to claim 8, wherein the thickness of the cured coating film is from 50 to 300 nm.

* * * * *